United States Patent [19]

Henkens et al.

[11] Patent Number: 5,225,064
[45] Date of Patent: Jul. 6, 1993

[54] PEROXIDASE COLLOIDAL GOLD OXIDASE BIOSENSORS FOR MEDIATORLESS GLUCOSE DETERMINATION

[75] Inventors: Robert W. Henkens, Durham; Junguo Zhao, Chapel Hill; John P. O'Daly, Carrboro, all of N.C.

[73] Assignee: Enzyme Technology Research Group, Inc., Durham, N.C.

[21] Appl. No.: 846,229

[22] Filed: Mar. 6, 1992

Related U.S. Application Data

[63] Continuation-in-part of Ser. No. 821,732, Jan. 15, 1992.

[51] Int. Cl.$^5$ .............................................. G01N 27/26
[52] U.S. Cl. .................................... 204/403; 204/415; 435/817
[58] Field of Search ................. 204/403, 415; 435/817

[56] References Cited

U.S. PATENT DOCUMENTS

| | | | |
|---|---|---|---|
| 4,340,448 | 7/1982 | Schiller et al. | 204/403 |
| 4,820,399 | 4/1989 | Senda et al. | 204/403 |
| 4,970,145 | 11/1990 | Bennetto et al. | 204/403 |
| 5,082,550 | 1/1992 | Rishpon et al. | |
| 5,082,786 | 1/1992 | Nakamoto | |

OTHER PUBLICATIONS

Crumbliss, A. L. et al., "Catalytic and Electroactivity of Irreversibly Adsorbed Enzymes at Gold Electrode Surfaces," Symposium on Protein Electrochemistry: Abstract for the ACS Southeast Regional Meeting (SERM) Oct., 1989, published in USA.
Fair, B. D., and Jamieson, A. M., "Studies of Protein Adsorption on Polystyrene Latex Surfaces," *J. Colloid Interface Sci.*, 77(2):525–534, 1980.
Frew, J. E. et al., "A Method for Estimation of Hydrogen Peroxide Based on Mediated Electron Transfer Reactions of Peroxidases at Electrodes," *Electroanal. Chem.*, 201:1, 1986.
Govindaraju, K. et al., "Active Site Chemistry of Lysyl Oxidase," *J. Inorg. Biochem.*, 29:111, 1987.
Gregg, B. A., and Heller, A., "Cross-Linked Redox Gels Containing Glucose Oxidase for Amperometric Biosensor Applications," *Anal. Chem.*, 62:258–263, 1990.
Guo, L-H et al., "Direct Electrochemistry of Proteins and Enzymes," *Adv. Inorg. Chem.*, 36:341-375, 1991.
Guo, L-H et al., "Direct Voltammetry of the *Chromatium vinosum* Enzyme, Sulfide: Cytochrome c Oxidoreductase (Flavocytochrome c552)," *J. Biol. Chem.*, 265(4):1958–1963, 1990.
Guo, L-H et al., "Direct Un-Mediated Electrochemistry of the Enzyme p-Cresolmethylhydroxylase," *J. Electroanal. Chem.*, 266:379–396, 1989.
Hagen, W. R., "Direct Electron Transfer of Redox Proteins at the Bare glassy Carbon Electrode," *J. Biochem.*, 182:523–530, 1989.
Albery et al., "Inhibited Enzyme Electrodes. Part 3. A Sensor for Low Levels of H$_2$S and HCN," *Biosensors & Bioelectronics*, 5:397–413, 1990.
Armstrong, Fraser A., "Voltammetry of Metal Centres in Proteins," *Perspectives on Bioinorganic Chemistry*, 1:141–165, 1991.
Armstrong, F. A., and Lannon, A. M., "Fast Interfacial Electron Transfer between Cytochrome c Peroxidase and Graphite Electrodes Promoted by Aminoglycosides: Novel Electroenzymic Catalysis of H$_2$O$_2$ Reduction, " *J. Am. Chem. Soc.*, 109:7211–7212, 1987.

(List continued on next page.)

*Primary Examiner*—John Niebling
*Assistant Examiner*—Bruce F. Bell
*Attorney, Agent, or Firm*—Arnold, White & Durkee

[57] ABSTRACT

Horseradish peroxidase (HRP) immobilized on colloidal gold and then deposited on an electrode surface can be reduced at a convenient rate at low voltage (Ag-/AgCl) without an electron transfer mediator. Bioelectrodes combining both a colloidal gold-adsorbed oxidase and colloidal gold-adsorbed HRP located on an electrode surface are efficient biodetectors, particularly for the measurement of low glucose levels in samples when glucose oxidase is employed as the sensing enzyme. The biodetectors may be employed for mediatorless detection of a wide variety of analytes depending on the oxidase employed.

15 Claims, 6 Drawing Sheets

OTHER PUBLICATIONS

Bowden, E. F., and Hawkridge, F. M., "Interfacial Electrochemistry of Cytochrome c At Tin Oxide, Indium Oxide, Gold, and Platinum Electrodes," *J. Electroanal. Chem.*, 161:355-376, 1984.

Cass, A. E. G., ed., Biosensors: A Practical Approach, Oxford University Press, Oxford/New York, 1990.

Crumbliss, A. L. et al., "Amperometric Glucose Sensor Fabricated from Glucose Oxidase and a Mediator Co-Immobilized on a Colloidal Gold Hydrogel Electrode," Abstract for the ACS North Carolina Divisional Meeting, University of North Carolina at Chapel Hill, Sep. 7-9, 1989, published in USA.

Crumbliss, A. L. et al., "The Use of Inorganic Materials to Control or Maintain Immobilized Enzyme Activity," Symposium on "opportunities for inorganic chemistry in biotechnology," Abstract for the ACS National Meeting in Boston, Apr. 23, 1990, published in USA.

Crumbliss, A. L. et al., "The Influence of Colloidal Gold Surfaces on Enzyme Activity," Abstract for the ACS North Carolina Divisional Meeting, Sep., 1988, published in USA.

Hale, P. D., et al., "Amperometric Glucose Biosensors Based on Redox Polymer-Mediated Electron Transfer," *Anal. Chem.*, 63:677-682, 1991.

Henkens, R. W. et al., "Bioactive Electrodes Using Metallo-Proteins Attached to Colloidal Gold," *Rec. Trav. Chem. Pays Bas.*, 106:6-7, 1987.

Henkens, R. W. et al., "Biosensor Electrodes Using Colloidal Gold Supported Oxidase Enzymes," *J. Inorg. Biochem.*, 43:120, 1991.

Henkens, R. W., and O'Daly, J. P., "Multi-Analyte Enzyme Electrodes for Environmental Monitoring," Abstract for the Proceedings of *5th International Biotechnology Conference* in Copenhagen, Jul. 8-13, 1990.

Jönsson, G., and Gorton, L., "An Electrochemical Sensor for Hydrogen Peroxide Based on Peroxidase Adsorbed on a Spectrographic Graphite Electrode," *Electroanalysis*, 1:465-468, 1989.

Kinoshita, Kim, "Carbon: Electrochemical and Physicochemical Properties," John Wiley & Sons, New York, 1988.

Paddock, R. M., and Bowden, E. F., "Electrocatalytic Reduction of Hydrogen Peroxide via Direct Electron Transfer from Pyrolytic Graphite Electrodes to Irreversibly Adsorbed Cytochrome c Peroxidase," *J. Electroanal. Chem.*, 260:487-494, 1989.

PEROXIDASE COLLOIDAL GOLD OXIDASE BIOSENSORS FOR MEDIATORLESS GLUCOSE DETERMINATION

This is a continuation-in-part of U.S. patent application Ser. No. 07/821,732 filed Jan. 15, 1992 which is incorporated by reference herein.

BACKGROUND OF THE INVENTION

1. Field of the Invention

The invention relates to peroxidase colloidal gold biosensors that provide a detectable electrochemical response based on direct oxidation of a redox protein at an electrode surface. In particular, mediatorless detection of glucose is possible with colloidal gold adsorbed horseradish peroxidase in the presence of glucose oxidase. The invention also includes methods of mediatorless detection of various analytes and processes for the preparation of colloidal gold adsorbed peroxidase based bioelectrodes.

2. Description of Related Art

Direct electron transfer between an enzyme and an electrode surface is of practical as well as theoretical interest. An enzyme capable of direct electron transfer immobilized on an electrode permits electrochemical measurement of the enzyme substrate without addition of a mediator to the analyte solution. Unfortunately, a serious problem with protein electrochemistry is the slow mass transport process and strong adsorption of protein molecules onto the electrode surface.

Because of the tendency of protein molecules to adsorb to surfaces, direct electron transfer to or from the electrode surface is possible only for the first layer of protein on the electrode. Even assuming a monolayer coverage and completely reversible electrochemistry between the adsorbed monolayer and the electrode surface, direct electron transfer between an adsorbed monolayer of redox protein and an electrode surface would result in a current approximately one-half that of the charging current.

While there are some examples of detectable electrochemical response based on direct oxidation of a redox protein at an electrode surface, detection has been difficult (Joensson and Gorton, 1989; Bowden et al., 1984). Amplification of the signal can in some cases be achieved by adding enzyme substrate.

Generally, in order to detect a signal, substrate is added in order to induce enzyme turnover (Guo and Hill, 1991). This significantly amplifies the signal which otherwise is generally too weak to be detected. A few limited examples showing direct electron transfer between various enzymes and electrode surfaces include cytochrome c peroxidase (Armstrong and Lannon, 1987), p-cresolmethylhydroxylase (Gou and Hill, 1989), and cytochrome $c_{552}$ (Guo and Hill, 1990) at surface-modified electrodes or in the presence of promoters. Other examples include cytochrome c peroxidase irreversibly adsorbed on pyrolytic graphite (Paddock and Bowden, 1989), and lysyl oxidase (Govindaraju et al., 1987) and horseradish peroxidase (Joensson and Gorton, 1989) on spectrographic graphite.

Current theories of non-mediated electrochemistry of proteins and enzymes emphasize the importance of the electrode surface in facilitating direct electron transfer (Guo and Hill, 1991). It has also been suggested that direct electron transfer may proceed most easily to/from electrode surfaces which provide an environment similar to the native environment of the redox protein (Armstrong, 1991). However, there has been limited success with approaches that deposit the redox protein directly on the surface, presumably because of protein denaturation.

Horseradish peroxidase (HRP) has been suggested and studied as a bioelectrode. An HRP electrode has high specific activity for $H_2O_2$ with each $H_2O$ molecule effectively converting ca. 25,000 $H_2O_2$ molecules to $H_2O$ per minute. In the presence of $H_2O_2$, HRP is efficiently converted to its oxidized form, $HRP_{ox}$ (reaction (1)) (Frew et al., 1986). This can then be reduced, as shown in reaction (2), either directly or through an electron transfer mediator acting as an electron shuttle (Frew et al., 1986).

$$H_2O_2 + HRP_{red} \rightarrow HRP_{ox} + H_2O \qquad (1)$$

$$HRP_{ox} + 2e^- \rightarrow HRP_{red} \qquad (2)$$

While electrodes based on horseradish peroxidase will demonstrate direct electron transfer (Joensson and Gorton, 1989), a major problem in developing a redox system utilizing HRP has been to induce the heterogeneous electron transfer step (reaction step 2) to proceed at a reasonable rate. Acceptable rates of transfer are obtained in the presence of a mediator, but without a mediator the rates are too slow to be of practical value.

Biosensors are of particular interest for measuring glucose and there are biosensors utilizing glucose oxidase as the sensing enzyme. A glucose sensor based on gel immobilized glucose oxidase detects changes in pH when coimmobilized with gluconolactase which hydrolyzes the lactone product of glucose oxidation (Nakamoto, 1992). This type of glucose is, however, relatively insensitive to glucose levels below about 0.1 mM.

More sensitive enzyme electrochemical sensor electrodes have been developed that employ polymeric surface coatings. An enzyme such as glucose oxidase dispersed in the polymer facilitates detection of hydrogen peroxide produced during the reaction when employing a system incorporating a reference/counter electrode with the enzyme-coated electrode (Rishpon et al., 1992).

As a general principle, in the operation of a glucose biosensor, glucose oxidase is reduced during the oxidation of glucose; the reduced enzyme is then reoxidized either through an electron transfer mediator, which itself becomes reoxidized on the electrode surface, or through molecular oxygen present in the solution. The product resulting from oxygen reduction is hydrogen peroxide which can be reoxidized at the electrode at high positive potential, or, reduced to water at a high negative potential. In either case, a high background signal is generated with high risk of interferences from the sample matrix.

On the chemical level, a glucose biosensor is based on the conversion of glucose (GO, the substrate or analyte) to gluconolactone (GL) in the presence of a catalyst, glucose oxidase (GOD), represented by the following equation:

$$GO + GOD \rightarrow GL + GOD_{red} \qquad (3)$$

In order to maintain continuous oxidation of GO, $GOD_{red}$ has to be reoxidized to GOD. Equations 4-6 represent three different paths for recycling GOD.

$$GOD_{red} - 2e^- \rightarrow GOD \quad \text{(4) on an electrode surface}$$

$$GOD_{red} + O_2 \rightarrow GOD + H_2O_2 \quad \text{(5) molecular oxygen}$$

$$GOD_{red} + MED_{ox} \rightarrow GOD + MED_{red} \quad \text{(6) added electron transfer agent}$$

The added electron transfer agent or mediator may be reoxidized as shown in equation (7)

$$MED_{red} - e^- \rightarrow MED_{ox} \quad (7)$$

Hydrogen peroxide generated from reduction of molecular oxygen will react, depending on conditions, in the reduction mode, equation (8), or in the oxidation mode, equation (9).

$$H_2O_2 + 2\,e^- + 2\,H \rightarrow 2\,H_2O \quad \text{(8) reduction mode}$$

$$H_2O_2 - 2\,e^- \rightarrow O_2 + 2\,H^+ \quad \text{(9) oxidation mode}$$

The process represented by equation (4) is normally very slow and therefore considered impractical. The reaction with molecular oxygen, equation (5), will take place unless oxygen is purged from the system. Mediated reactions, represented by equation (6), can be quite efficient, depending on the mediator.

For purposes of developing a practical glucose biosensor, three options would include, based on equations 3-9:

Mode one: (3)→(6)→(7): oxidation mode;
Mode two: (3)→(5)→(9): oxidation mode; and
Mode three: (3)→(5)→(8): reduction mode Mode one operates at a potential of 0.3-0.4 V and has the advantage of being a direct measure of the glucose oxidase redox process. There are, however, several disadvantages, including requirement of a mediator which to be effective must be immobilized near the electrode surface. The effectiveness, operational potential (0.3-0.4V/Ag/AgCl) and the background current depend on the mediator. Moreover, the mediator must be initially in its oxidized form in order to minimize the initial background current. Unfortunately, good mediators, e.g., ferrocene and its derivatives, are only readily available in their reduced form.

Yet another disadvantage of Mode one operation is sensitivity to molecular oxygen. $O_2$, when present, will compete with the mediator. As a practical matter, purging the oxygen is time-consuming and expensive in large scale operations. The effect of $O_2$ depends on the relative rate of the reactions shown in equations (5) and (6). A further disadvantage is the dependence of the $O_2$ effect on glucose concentration as well as the concentration of molecular oxygen present. Variation of ambient $O_2$ concentration therefore will have unpredictable effects on the mediated signal. Even at constant $O_2$ concentration, predictability is difficult because the effect is more detrimental at low glucose concentrations than at higher glucose concentrations (Hale et al., 1991; Gregg and Heller, 1990). At present, no mediators have been reported that operate efficiently enough to eliminate the oxygen effect.

Mode two operates at a potential of 0.6-0.7V and has several advantages, including the fact it is not sensitive to oxygen at low glucose concentrations as there is usually sufficient oxygen in the solution. Additionally, a mediator is not required and there are no competitive reactions, assuming no interfering substances are added in the sample.

Mode two does, however, have several disadvantages. The process is sensitive to oxygen at high glucose concentrations when oxygen which is normally present may become limited. The product, not the enzyme redox process, is measured. And the high operational potential, 0.6-0.7 V/Ag/AgCl, results in a high background current, so that the signal current may be difficult to detect.

Mode three operates at 0V Ag/AgCl and has a number of advantages. This system can be coupled to HRP with direct electron transfer in the reduction mode, equation (8), at 0V on the electrode. As in Mode two, no mediator is required, there are no competing reactions and there is no oxygen sensitivity at low glucose concentrations. A distinct advantage is low background and interference due to the low operational potential.

Mode three disadvantages include sensitivity to oxygen at high glucose concentrations and measurement of a product rather than the enzyme redox process directly. Additionally, two enzymes are required, adding complexity to the system and possible additional expense for fabrication.

Enzyme electrochemical sensors for glucose determination have been described (Rishpon et al., 1992). In these Mode one type biosensors, GOD is incorporated into membranes near the electrode surface to reduce interference from undesired oxidizable compounds and to reduce oxygen sensitivity. The electrode is however not sensitive to glucose concentrations below about 1 mM.

Electron transfer agents, such as ferrocenes, have been used in conjunction with glucose oxidase. However, two major drawbacks exist. In common practice, electron transfer mediators are small molecules, typically ferrocene for glucose oxidase based biosensors. It is generally desirable to immobilize a mediator to keep it close to the surface; however, small molecules are difficult to immobilize. A more difficult problem is the ubiquitous presence of molecular oxygen. Oxygen will always be reduced to some extent, even in the presence of a mediator. The result is that, while a mediated response may produce a satisfactory response to relatively high glucose concentrations, it is not feasible to measure low glucose (100 μM range) concentrations because of background current and the effect of oxygen.

SUMMARY OF THE INVENTION

The present invention addresses one or more of the foregoing problems in providing novel biosensors operating on direct electron transfer arising from reduction of a colloidal gold immobilized peroxidase deposited on a conducting surface. The bioelectrodes of the present invention when suitably coupled with a transducer are capable of detecting a current generated from reaction of hydrogen peroxide with the peroxidase on the conducting surface of the biosensor. Hydrogen peroxide, produced in the presence of oxygen during an oxidase catalyzed reaction of an appropriate substrate, efficiently oxidizes surface-deposited colloidal gold adsorbed peroxidases. The disclosed bioelectrodes prepared with colloidal gold adsorbed horseradish peroxidase and glucose oxidase are particularly suitable for determination of glucose. Current is produced in the presence of glucose at glucose concentrations as low as 1 μM. Other oxidases, such as alcohol oxidase, galactose oxidase, lactic acid oxidase, amino acid oxidase, cholesterol oxidase, xanthine oxidase and the like are also useful in practicing the invention so long as hydrogen peroxide is generated during the catalytic reaction.

The invention relates to novel colloidal gold based bioelectrodes employing an immobilized colloidal gold adsorbed peroxidase and at least one other enzyme in the oxidase class. In preferred practice, a bioelectrode is prepared from horseradish peroxidase which is first adsorbed onto colloidal gold sol particles and then deposited on a conducting electrode surface. One or more oxidase enzymes are then added prior to determination of selected analytes. The oxidase, selective for a particular analyte, may be added to a sample solution in soluble or immobilized form or, preferably, immobilized near or on the conducting surface where the peroxidase is deposited. Whether localized on or near the conducting surface, it is understood that the oxidase will be capable of coupling with HRP and as such to be "in communication" with a conducting surface so as to operate in the reduction mode (Mode three) previously herein described in equations (3), (5) and (8).

Horseradish peroxidase has a very specific activity toward hydrogen peroxide and is efficiently converted to its oxidized form. As disclosed herein, horseradish peroxide present on a conducting electrode surface can be efficiently reduced directly on the electrode surface at a voltage near 0 volts Ag/AgCl. This takes place through a direct electron transfer and does not require an electron transfer mediator. A novel aspect of the invention is the absorption of horseradish peroxidase on to the surface of colloidal gold particles prior to depositing the enzyme on a conducting electrode surface.

While the invention has been demonstrated with horseradish peroxidase, it is understood that other sources of peroxidases may also be employed, not necessarily limited to horseradish. Moreover, other peroxidase-type enzymes are contemplated as useful so long as the enzyme will accept hydrogen peroxide as a substrate. Depending on the particular bioelectrode desired, there are several properties to be considered. Properties such as enzyme stability, high specific activity, and efficient conversion of hydrogen peroxide are factors to consider. The invention need not be limited to immobilized native peroxidases. Genetically engineered, truncated enzymes including active catalytic sites, or modified catalytically active species may also be useful and even more efficient in some applications.

A second component of the disclosed bioelectrode includes an oxidase. As used herein, oxidase includes any enzyme that is capable of generating hydrogen peroxide during a catalytic reaction. The oxidase will be selected to catalyze a reaction with a desired analyte. By analyte is meant a substrate for the selected enzyme. A further constraint in forming an operable system is the presence of molecular oxygen which, during the catalytic reaction, will be converted to hydrogen peroxide which will oxidize colloidal gold adsorbed horseradish peroxidase located on the electrode surface. When appropriately combined with a reference/counter electrode, direct electron transfer occurs at the electrode surface resulting in regeneration of the reduced form of horseradish peroxidase.

Bioelectrodes of the invention are basically two-enzyme electrodes. A sensing enzyme, typically horseradish peroxidase, is adsorbed to the surface of colloidal gold sol particles. Adsorption to the surface of colloidal gold particles appears to stabilize the enzyme and to provide a conducting matrix. In practice, colloidal gold adsorbed HRP is deposited on a conducting electrode surface. Deposition may be through spraying, dipping, electrodeposition, solvent evaporation or a variety of other well-known techniques but is most conveniently accomplished by simply evaporating a colloidal gold adsorbed horseradish peroxidase solution onto the electrode surface. An oxidase is provided to detect a desired analyte. Examples of analytes include cholesterol, xanthine, monosaccharides such as glucose, amino acids and alcohols. The oxidase selected will, however, produce hydrogen peroxide during catalytic conversion of a desired analyte. The hydrogen peroxide produced is detectable by the peroxidase immobilized on the conducting electrode surface.

Enzymes employed in conjunction with horseradish peroxidase typically include oxidases. Such enzymes generate hydrogen peroxide from molecular oxygen in the course of the catalytic reaction. Preferred enzymes include cholesterol oxidase, amino acid oxidase, alcohol oxidase, lactic acid oxidase, galactose oxidase and, most preferably, glucose oxidase.

In yet another aspect of the invention colloidal gold adsorbed enzyme is first immobilized in a matrix which is then positioned at or near the electrode surface. Several types of matrix are suitable, including hydrophilic polymers such as the carrageenans, agar and similar hydrophilic gels. The selected matrix may be used merely to protect the surface of the gel, or alternatively as a second immobilization material in which, for example, colloidal gold adsorbed enzyme is dispersed. It is contemplated that more than one enzyme may be conveniently dispersed within a gel matrix. Appropriate alteration of the electrode potential when configured as a biosensor allows sequential determination of more than one analyte.

Another aspect of the present invention includes a method for enzyme electrochemical detection of a desired analyte. A bioelectrode as described herein is contacted with a sample that may contain the analyte of interest. Analyte present in the sample is determined from the amount of current generated from hydrogen peroxide reduction by peroxidase immobilized at the conducting surface. Hydrogen peroxide produced during the enzyme catalyzed analyte conversion is selectively reduced to water by horseradish peroxidase on the electrode surface. All electron transfers in the disclosed systems will operate without addition of electron transfer mediators, and will do so more efficiently than when mediators are present when the appropriate methods of preparation are employed. However, this does not preclude the use of a mediator if desired. In some configurations, the use of a mediator may offer more efficient transfer.

Analytes to be analyzed by the present invention may be found in a wide variety of aqueous samples including water, urine, blood, sweat, and other body fluids such as vaginal or seminal fluids. In a most preferred embodiment, a horseradish peroxidase/glucose oxidase bioelectrode will detect glucose by direct electron transfer.

Yet another aspect of the invention is a selective bioelectrode for the detection of glucose. Such a bioelectrode includes a first layer of colloidal gold-adsorbed horseradish peroxidase deposited on a conducting electrode surface and a second layer of colloidal gold-adsorbed glucose oxidase preferably overlying the first layer of colloidal gold-adsorbed HRP. A preferred conducting electrode surface is glassy carbon, although usable conducting surfaces include carbon, gold, platinum, and the like. In preferred practice both layers of colloidal gold adsorbed enzymes are evaporatively deposited onto a conducting surface. Typically, glucose oxidase immobilized on colloidal gold will be in contact with the colloidal gold adsorbed HRP. Glucose bioelectrodes constructed in this manner are capable of detecting glucose levels at least as low as 1 $\mu M$ and generally show a linear response to glucose concentrations as high as 250 $\mu M$.

Bioelectrodes convenient for detecting glucose are typically constructed as biosensors by combining with reference and counter electrodes. Samples containing glucose or suspected of containing glucose are contacted with the bioelectrode and the amount of current produced is related to the amount of glucose present. Current is produced by reduction of hydrogen peroxide at the conducting surface of the bioelectrode and is typically measured at 0 volts/Ag versus Ag/AgCl.

A novel aspect of the present invention is the capacity of the disclosed bioelectrodes to amperometrically detect a selected analyte by direct electron transfer at the electrode surface without the need for an electron transfer mediator. Surface contact of the detecting enzyme, typically horseradish peroxidase, and, surprisingly, the coating distribution of the enzyme on the surface of the colloidal gold particles contribute to the reactivity and response of the electrode. In general, monolayer coverage of the colloidal gold particle surface by HRP appears to provide the most effective electron transfer without a mediator. This does not preclude effective mediatorless electron transfer with less than monolayer coverage or even imperfect or partial coatings. This likely depends on the enzyme adsorbed to the colloidal gold as well as the properties, e.g. size, of the sol particles to some extent. Additional layers of HRP on the surfaces of colloidal gold particles, at least where a glucose bioelectrode is concerned, do not increase response. Surface coverage significantly greater than monolayer may generally inhibit direct electron transfer response.

DETAILED DESCRIPTION OF PREFERRED EMBODIMENTS

Figure 1:
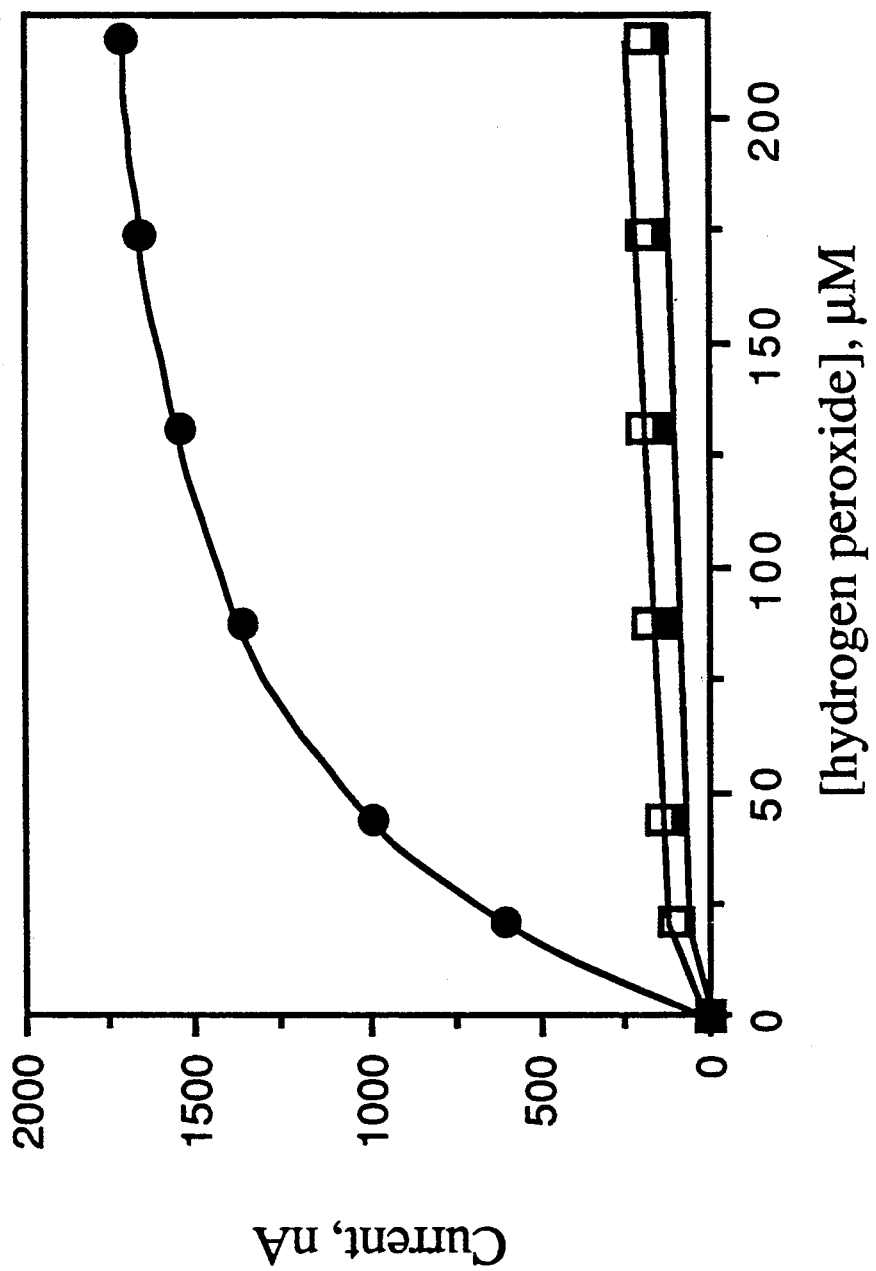
FIG. 1 shows the steady-state amperometry measurement of current vs. peroxide concentration in stirred buffer with or without 0.2 mM ferrocenecarboxylic acid mediator at 0V/Ag. ■ ) HRP solution evaporated onto glassy carbon without mediator; □ ) HRP solution evaporated onto glassy carbon with a mediator in solution; ● ) Au-HRP sol evaporated onto glassy carbon without a mediator.

The electrochemistry associated with redox enzymes and low molecular weight proteins attached to electrode surfaces has become an important and well-established area of research (Cass, 1986 . Most reports in the literature describe the electrochemistry of small redox proteins such as cytochrome c (Albery et al., 1981) and ferredoxin (Hagen, 1989), generally on surface-modified electrodes, or mediated electron transfer between an enzyme and an electrode surface (e.g., glucose oxidase on a graphite electrode with a ferrocene derivative used as mediator (Cass et al., 1990)).

Colloidal gold has been used as an immobilization support for proteins employed as markers for electron microscopy. Under these conditions, the biological macromolecules are known to retain biological activity. It has been shown that several enzymes maintain their enzymatic and electrochemical activity when immobilized on colloidal gold (Henkens et al., 1987). The immobilization of a redox enzyme on colloidal gold may help the protein assume a favored orientation and/or provide conducting channels between prosthetic groups and the electrode surface. In either situation, effective electron transfer distance is reduced, thereby facilitating charge transfer.

Although it is contemplated that any of a number of peroxidases may be employed as an electron transfer enzyme at the conducting surface of the bioelectrode, horseradish peroxidase is particularly preferred and has been used to demonstrate the invention. Horseradish peroxidase (HRP) is available in pure form with very high specific activity, and has been successfully immobilized on colloidal gold with retention of its biological activity (Henkens et al., 1991). The mediated reduction of immobilized HRP occurs at 0V (Ag/AgCl) at a reasonable rate.

The reduction of native HRP to its ferrous form at modified electrodes is effected at relatively high negative potentials (−0.71V/SCE). The reduction of oxidized HRP (eq. 2) to its native state will proceed in the absence of a mediator at a glassy carbon electrode as well as in the presence of the mediator ferrocenecarboxylic acid (Frew et al. 1986). This demonstrates the thermodynamic possibility of direct reduction of HRP on the electrode surface near 0 V/Ag. In the absence of an electron transfer mediator, current measured by cyclic voltammetry or steady-state amperometry using an HRP modified electrode in the presence or absence of $H_2O_2$ is an indication of direct HRP reduction.

High background current problems associated with mediated electron transfer of glucose oxidase at the electrode are overcome with the use of horseradish peroxidase as part of a dual enzyme electrode for sensing low concentrations of analytes. Horseradish peroxidase may be co-immobilized for peroxide reduction at ideal potentials (0V vs Ag/AgCl). Background and interferences from the sample matrix are eliminated or greatly reduced. A dual enzyme HRP/glucose oxidase electrode will be less sensitive to oxygen and variations in oxygen concentration at low glucose concentrations with less effect on the signal current than at higher concentrations of glucose.

Materials and Methods

HRP, type VIA, was purchased from Sigma Chemical Co. (St. Louis, Mo.) and dialyzed before use against 2 mM sodium phosphate at pH 7.0 or used directly without further treatment.

Gold trichloride ($HAuCl_4.3H_2O$) was purchased from Fisher Chemical Co.; ferrocenecarboxylic acid was from Aldrich.

Preparation of Gold Sols

Gold sols were prepared with a particle diameter of approximately 30 nm. A solution of 0.3% aqueous sodium citrate was added to a boiling rapidly stirred solution of 0.01% gold trichloride and the solution refluxed for 30 min. The final concentrations (w/v) were 0.01% $HAuCl_4$ and 0.03% sodium citrate. The particle size was estimated by filtration of the sol through polycarbonate membranes (Nuclepore Corp.) of varying pore sizes using an Amicon micro ultrafiltration unit. Approximately 40% of the sol passed through a 500 Å Nuclepore filter and was quantitatively collected on a 300 Å Nuclepore filter.

Preparation of Colloidal Gold Adsorbed Enzyme

The gold sol was concentrated by centrifugation at room temperature. The concentrated sol was mixed with appropriate amounts of HRP and a fixed amount of the Au-HRP sol evaporated on a coplanar carbon electrode surface. HRP concentration in the sol measured against electrode activity was used to determine optimum composition of the Au-HRP sol.

Electrodes

Glassy carbon electrodes were prepared by inserting a glassy carbon rod into a hot, soft teflon cylinder with a copper or stainless steel rod connection. On cooling, the teflon became tightly wrapped around the glassy carbon rod. Silver epoxy served to connect the metal with the glassy carbon.

Coplanar glassy carbon electrodes were prepared by first wrapping a glassy carbon rod with heat shrinkable tubing. A silver wire served as a reference electrode and a platinum foil as a counter electrode, each wrapped with additional heat shrinkable tubing with at least one layer of insulating tubing between each of the three electrodes. All three electrodes were exposed on the same surface.

Two electrode materials were used to prepare four different HRP or HRP colloidal gold (HRP-Au) modified electrodes. One consisted of three vapor deposited gold strips on glass (Au/glass). Silver was electroplated onto one of the strips as the reference electrode. HRP solution or HRP-Au sol (3 μl) was evaporated onto one of the strips to make the HRP-Au or HRP modified working electrode. The remaining bare strip served as the auxiliary electrode. The second HRP electrode configuration consisted of a glassy carbon working electrode, Ag/AgCl reference and Pt wire auxiliary electrode. HRP-Au sol or HRP solution was evaporated onto the working electrode. Three-electrode cells were used with 5 mL sample size. The HRP coated electrode surfaces had an area of about 7 $mm^2$.

The buffer solution was 50 mM phosphate at pH 6.8 with 10 mM KCl unless otherwise specified. No deaeration was necessary in most cases. In mediated experiments, ferrocenecarboxylic acid was used at a concentration of 0.20 mM, which is well into the region where the electrode response is independent of the mediator concentration.

A Pine Instrument RD4 bi-potentiostat interfaced to an IBM-386 computer was used for the measurements. The system was controlled with ASYST programs, and electrochemical data were directly collected and processed in the computer. Cyclic voltammograms were obtained without stirring the solution. In steady-state amperometry experiments the potential was set at 0V/Ag in stirred buffer, and the steady state current was measured.

Although there are examples in the literature of direct electron transfer between a redox protein and an electrode, facile transfer of electrons has generally been considered difficult with a non-functionalized electrode surface. HRP adsorbed on flat Au/glass did not respond to $H_2O_2$ unless an electron transfer mediator was present, indicating the lack of direct reduction of HRP. However, when HRP was adsorbed to a colloidal gold sol and then deposited on glassy carbon (FIG. 1 (●)) or a flat metal surface (FIG. 2 (●)), direct reduction of HRP on the electrode surface was observed.

Figure 2:
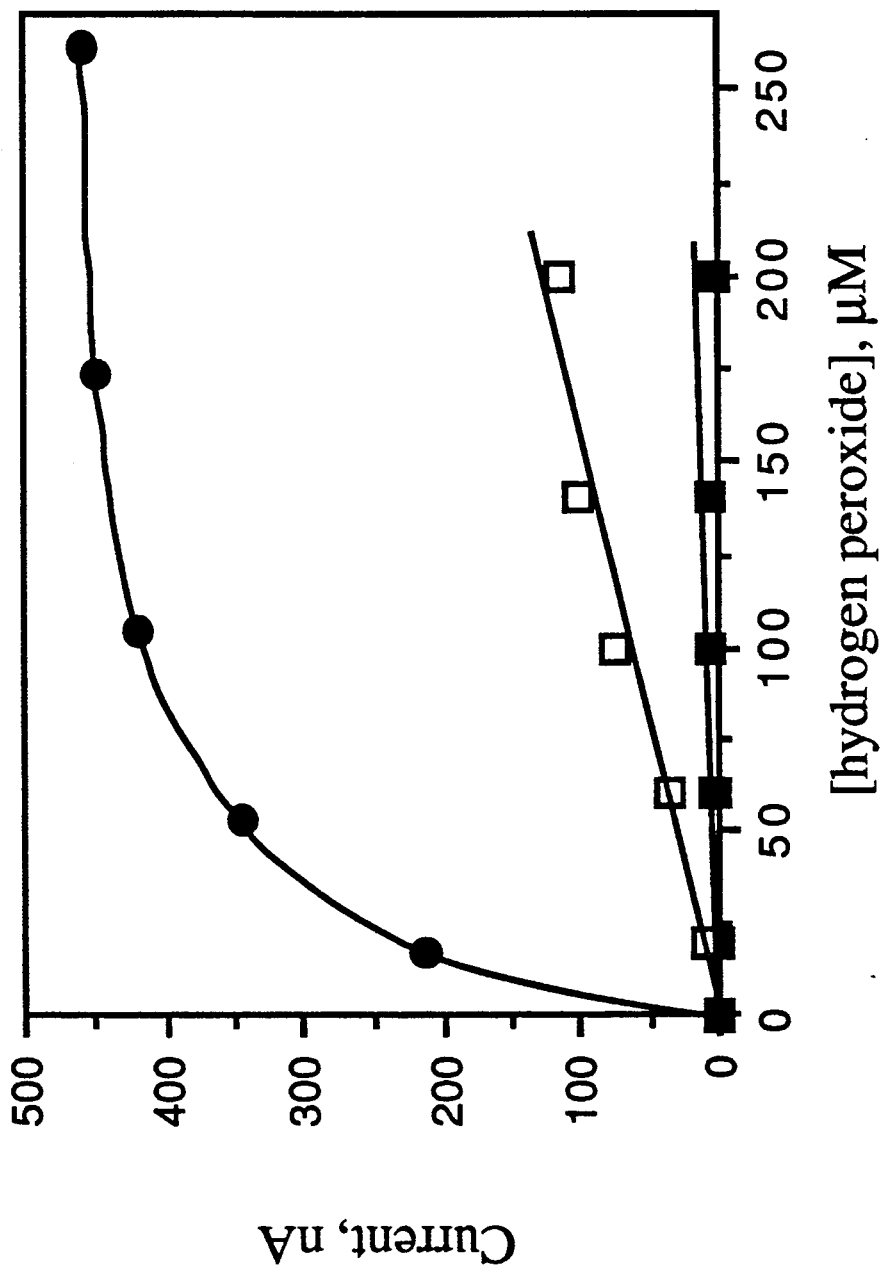
FIG. 2 is the same measurement as in FIG. 1 except that colloidal gold immobilized HRP was deposited on a gold film over a glass electrode surface rather than on glassy carbon.

A freshly polished glassy carbon surface has many functional groups, so that in a sense a chemically modified surface is exposed to the solution (Kinoshita, 1989). The functional groups may act as absorption sites which promote electron transfer. HRP adsorbed onto freshly polished glassy carbon catalyzed reduction of $H_2O_2$ without a mediator (FIG. 1, ■). Gold film surfaces, which do not have functional groups such as are found on the surface of glassy carbon, did not catalyze the direct reduction of $H_2O_2$(FIG. 2, ■). Reduction proceeded reasonably well in the presence of a mediator (FIG. 2, □).

Electrodes prepared by deposition of a HRP-Au sol onto glassy carbon (FIG. 1 (●) or onto Au on glass (FIG. 2 (●)) responded to $H_2O_2$ in a stir-rate dependent manner at low peroxide concentrations (<50 μM $H_2O_2$) In this region of the curve the reaction was mainly diffusion controlled so that diffusion of the substrate to the electrode surface was the rate-limiting step.

At high peroxide concentrations (>150 μM $H_2O_2$) the response was enzymatically controlled, indicated by the lack of dependence on stirring rate. In this region of the curve, addition of mediator to the analyte solution increased the response significantly, i.e., addition of a mediator extended the linear range. This may arise because some of the colloidal gold adsorbed HRP molecules are not in an appropriate orientation for direct electron transfer. Addition of a mediator allows more of the adsorbed HRP molecules to participate in the electron transfer reaction, increasing the response.

Under optimum conditions when HRP coatings on the colloidal gold particle surfaces are equivalent to a monolayer coverage or less, there are no apparent mediator effects and the direct electron transfer if proportional to HRP loading.

For simple absorption of HRP on a glassy carbon electrode it may be assumed that only the first layer of the adsorbed HRP molecules accepts electrons directly from the electrode surface. Direct electron transfer from the electrode surface to the second layer and beyond may be neglected due to the long electron transfer distances involved and the specific orientations required for electron hopping or self exchange to occur. However, the presence of an electron transfer mediator should promote efficient charge transfer beyond the first layer. The observation that addition of mediator gives only a small increase in catalytic current in the case of simple absorption on a flat glassy carbon surface (FIG. 1, □) indicated that no more than a monolayer of HRP was adsorbed on the surface. Determination of the amount of adsorbed protein based on the total enzymatic activity of HRP on the electrode indicated that the surface coverage was <5% of a monolayer. The small increase in signal upon addition of a mediator also implied that most of the adsorbed protein molecules had good access to electrode surface functional groups. The absorption appeared to be specific and uniform.

A colloidal gold surface is very different from flat bulk gold. Although the exact nature of the colloidal gold/protein/electrode surface interaction has not been completely defined, there are several ways in which colloidal gold may be visualized as assisting in electron transfer between a redox protein and an electrode surface. Colloidal gold particles have high surface to volume ratios. Uncontaminated gold sol particle surfaces have high surface energy and so are very active. The interaction with protein molecules can be very strong. The small size of the colloidal gold particles (approximately 30 nm) gives the protein molecules more freedom in orientation thus increasing the possibility that the prosthetic group is closer to the metal particle surface. The distance between the protein and the metal particles is shorter, facilitating charge transfer. When colloidal gold adsorbed HRP is deposited onto an electrode surface, HRP coated colloidal gold particles function as electron-conducting pathways between the prosthetic groups and the electrode surface.

The larger effective surface area of a colloidal gold particle may allow more enzyme molecules to be immobilized at or near the electrode surface. The possibility for multilayers of effective Au-HRP layers may be another mechanism by which the signal from colloidal gold assisted immobilization is increased. However, the effective layer should not be too deep because the signal does not increase proportionally with the amount of HRP-Au sol deposited (1–10 μl on a 3 mm diameter glassy carbon surface), with or without an electron transfer mediator. Unmediated electron transfer decreases when the deposited HRP-Au layer is too thick, probably because interior enzyme-Au layers are less efficient conductors than glassy carbon.

Assuming that the average diameter of the sol particle is 30 nm and the density is 17.0 g/ml, then 3 μl of 7.5 mg Au/ml sol deposited onto a glassy carbon surface of 3 mm in diameter is equivalent to about 12 layers of Au sol particles. This surface coverage gives the best performance, both with or without a mediator. Additional Au layers cause some deterioration in unmediated response but there is little effect on mediated response. This suggests that the deposited Au layers are not very porous and that the accessible depth is about 12 layers of deposited Au sol. Even within the 12 layers, only the outermost layers are important, because changing from 4 to 12 layers increased the signal by only 10–20% with or without a mediator. In consideration of both the electrode performance and cost, 3 μl HRP-Au sol is optimum for a 3 mm diameter glassy carbon surface.

Although only the outermost gold layers appear to contribute the major portion of the accessible enzyme molecules, enzyme loading and mediator effects with colloidal gold assisted immobilization are significantly higher when compared with simple absorption on surfaces. Spectroscopic data for the enzymatic activity of HRP adsorbed on colloidal gold before deposition on the electrode surface indicate that the active enzyme coverage on the gold sol particle surfaces is about 40% of a theoretical compact monolayer. This is consistent with absorption of γ-globulin onto latex particles (Fair and Jamieson, 1980). Multilayer absorption of protein molecules on a solid support surface is likely negligible. If absorption is not specific, protein molecules may have multiple orientations on the surface. The strong interactions between the protein and the Au sol surface may increase the surface density of the adsorbed protein, and some of the restricted orientations may also favor direct electron transfer between protein molecules and the conductor surface. It is likely that all of the active enzyme molecules are on the first layer of the adsorbed surface, but only part of the molecules have the correct orientation for direct electron transfer.

EXAMPLE 1

This example illustrates that colloidal gold adsorbed HRP deposited onto a glassy carbon surface produces an excellent electrode response to hydrogen peroxide without a mediator. Colloidal gold or HRP alone elicited either no response or a very low response.

Colloidal Gold Deposited on Electrode Surface

Colloidal gold sols were prepared and evaporated onto glassy carbon or Au/glass surfaces. None of the electrodes tested had a significant response to $H_2O_2$ (up to 200 μM) in steady-state amperometry measurements at 0V/Ag. The sensitivity was <0.05 nA/μM $H_2O_2$ in the presence or absence of ferrocenecarboxylic acid. Electrodes prepared from colloidal gold deposited on glassy carbon showed no catalytic current in cyclic voltammograms recorded with 0 to 2 mM $H_2O_2$.

HRP Deposited on Electrode Surface

Aliquots of a solution of HRP in buffer with no colloidal gold were evaporated onto the surface of Au-glass or glassy carbon electrodes and the response of these electrodes to $H_2O_2$ measured by steady-state amperometry. The HRP/glassy carbon electrode showed a low response to $H_2O_2$ in the absence of an electron transfer mediator (FIG. 1, ■). Addition of ferrocenecarboxylic acid slightly increased the response to $H_2O_2$ (FIG. 1, □). The HRP/Au/glass electrode gave very little response to $H_2O_2$ in the absence of ferrocenecarboxylic acid (FIG. 2, ■), but gave an improved response in the presence of the mediator (FIG. 2, □).

Colloidal Gold-HRP Deposited on Electrode Surface

Electrodes were prepared by evaporating HRP-Au sols onto glassy carbon or Au/glass surfaces. FIG. 1 (●) illustrates a strong response of the HRP-Au sol/glassy carbon (HRP-Au/C) electrode to varying concentrations of $H_2O_2$ in the absence of an electron transfer mediator. Steady state amperometric measurement of current was determined in stirred pH 6.8 buffer (50 mM phosphate, 10 mM KCl) with or without 0.2 mM ferrocenecarboxylic acid mediator at 0V/Ag. Electrode surface area was 7 mm².

FIG. 2 (●) illustrates a similar strong response in the absence of a mediator to varying $H_2O_2$ concentrations for electrodes prepared from deposition of colloidal gold adsorbed HRP onto Au/glass surfaces. For both electrode materials (glassy carbon and Au/glass) the HRP-Au sol modified electrodes, in the absence of a mediator, gave a better response to varying $H_2O_2$ concentrations than electrodes prepared without colloidal Au, even in the presence of a mediator. This may be due in part to the larger amount of HRP immobilized on the high surface area colloidal gold particles than on flat electrode surfaces. From the enzymatic activity of the HRP-Au sol it was determined that the ratio of adsorbed HRP to Au was 35 mg HRP per g Au. The enzymatic activity per unit volume was slightly higher for the HRP solution used to prepare the HRP electrodes than for HRP on colloidal Au sol. The HRP may also adsorb more tightly to colloidal gold than to glassy carbon.

EXAMPLE 2

The effect of pH on HRP response at an electrode is shown in the following example.

pH Effect on Electrode Response

Electrodes were prepared by evaporatively depositing 3 $\mu$l of a colloidal gold adsorbed HRP sol onto a 3 glassy carbon (3 mm diameter) giving a surface coverage of about 7 mm$^2$.

Figure 4:
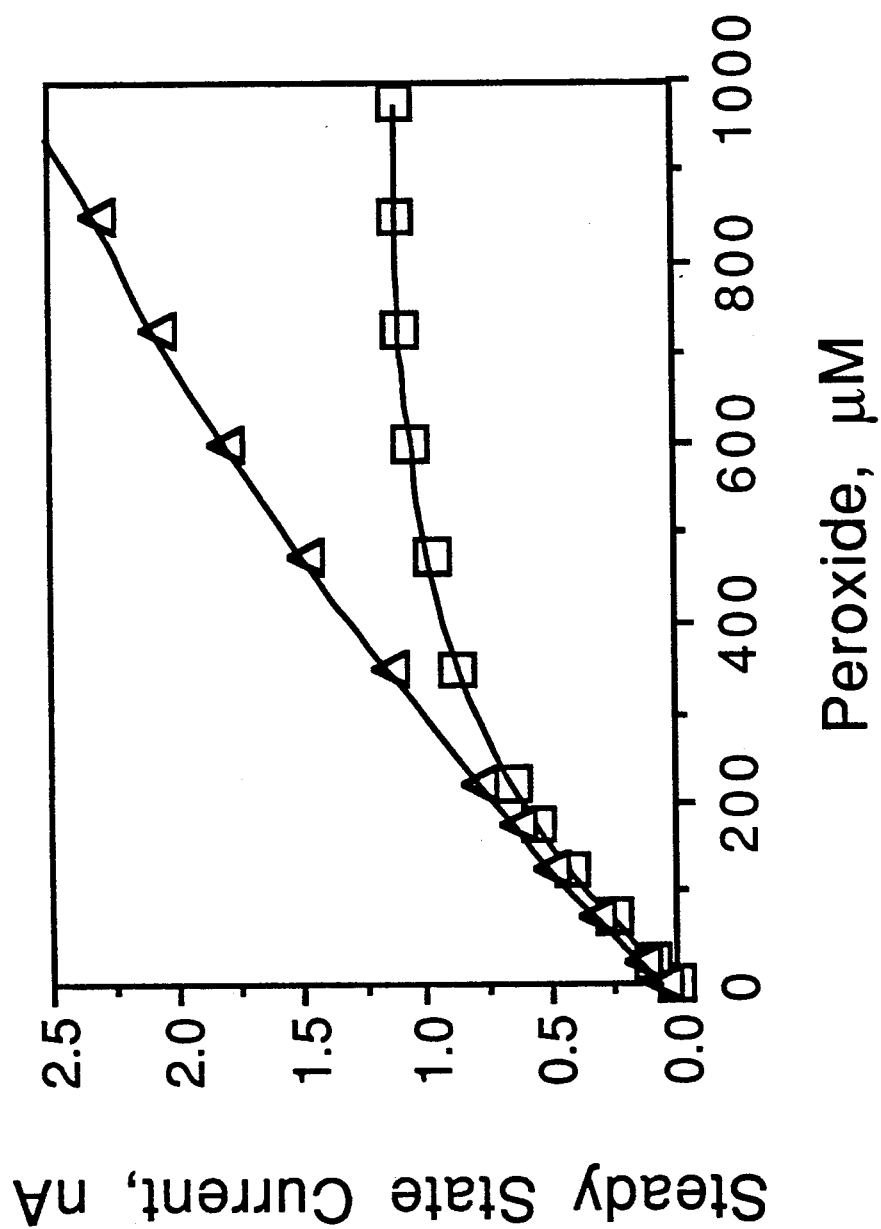
FIG. 4 shows a plot of steady state current in nA versus micromolar concentration of hydrogen peroxide for a colloidal gold/HRP electrode. Response in acetate, (Δ) and phosphate (□) buffers in the absence of an electron transfer mediator is shown.

The effect of pH on electrode response is shown in FIG. 4. Electrodes prepared by depositing colloidal gold adsorbed HRP onto glassy carbon showed a linear steady state current response to up to at least 800 $\mu$M peroxide in 0.05 M sodium acetate, pH 5.0, buffer containing 0.002 M KCl. Response was linear up to approximately 250 $\mu$M peroxide in 0.05 M sodium phosphate buffer, pH 7.0.

EXAMPLE 3

$H_2O_2$ response of HRP immobilized on the electrode surface was affected by the surface coverage of HRP on the colloidal particles. Response with and without a mediator was affected.

Effect of Gold Sol Surface Coverage on HRP Electrode Response

HRP electrodes, prepared in accordance with Example 2 were tested in 0.05M phosphate, pH 7.0, buffer and in 0.05M sodium acetate, pH 5.0, buffer at 0V/Ag/AgCl (2 mM KCl) with and without ferrocene monocarboxylic acid as electron transfer mediator. HRP/colloidal gold sols were evaporated on a glassy carbon surface using 2-3 1 to cover a 7 mm$^2$ surface area.

Surface coverage on colloidal gold particles was calculated assuming a sol particle diameter of 30 nm and a density of 17 g/ml, a diameter of 5 nm for HRP with a cross section area of 25 nm$^2$. Using these values, and adding different amounts of HRP for absorption to the sol particles, measurements of current signal vs peroxide concentrations showed that addition of the mediator ferrocene monocarboxylic acid did not affect the signal. The current signal was directly proportional to HRP-Au loading onto the sol particle surface up to the calculated monolayer coverage of HRP.

When sol surface coverage with HRP was in excess of one monolayer there was a reduction of the current signal. Addition of ferrocene carboxylic acid caused an increase in signal current. Results showed that a mediator had no effect on the signal current until colloidal gold particle surfaces were covered with HRP in excess of a monolayer. At higher loadings, presumably as the particles became coated with additional layers of colloidal gold adsorbed HRP, increasing "mediator effects" were observed. At the same time, direct electron transfer decreased.

EXAMPLE 4

Inhibition of Electrode Response

Figure 3:
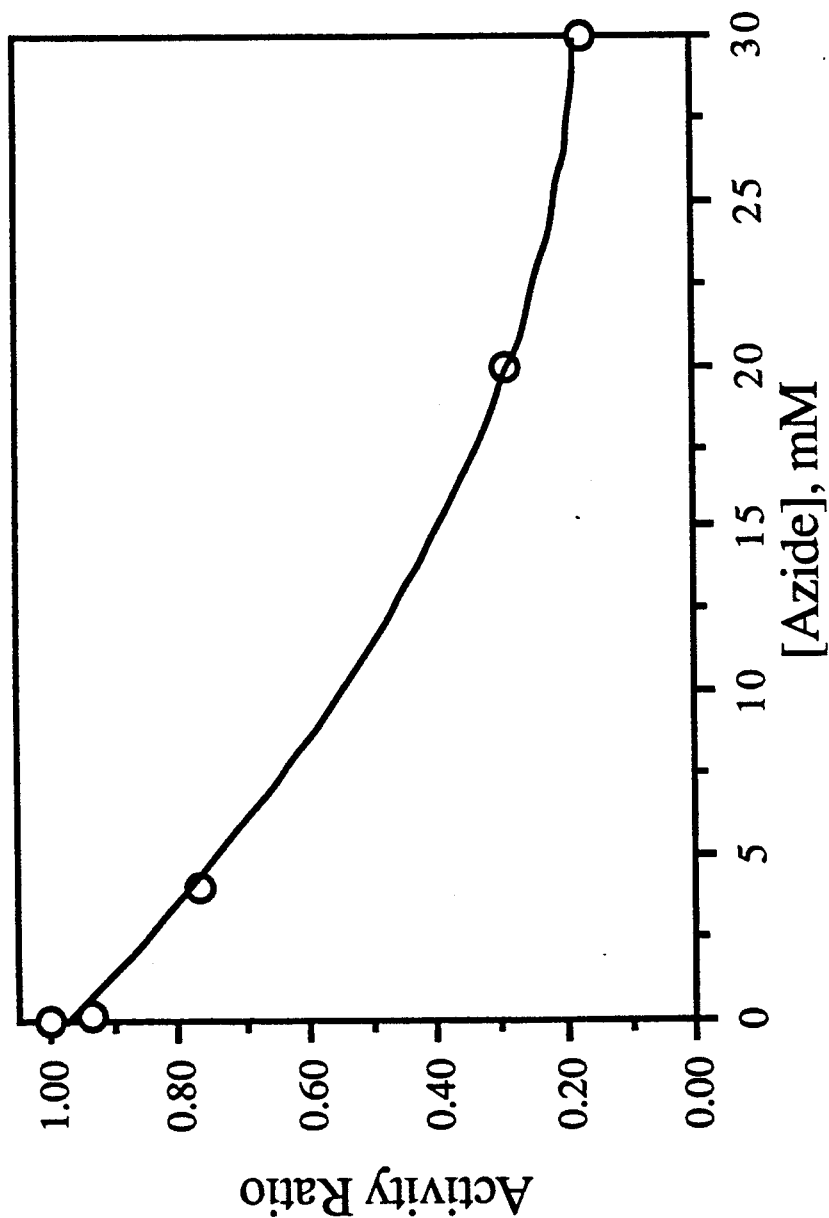
FIG. 3 is a plot of the activity ratio (electrode response in presence of azide/electrode response in absence of azide) vs. sodium azide concentration.

Sodium azide was added to the electrode prepared from HRP-Au. Measurements were made of the steady state current at 0V/Ag with a HRP-Au sol/glassy carbon electrode (HRP-Au/C) in stirred buffer in the presence and absence of the inhibitor. The analyte solution contained 50 mM potassium phosphate, 10 mM KCl, pH 6.8, 200–300 $\mu$M hydrogen peroxide and varying concentrations of sodium azide as indicated in FIG. 3. No mediator was present. As shown in FIG. 3, addition of sodium azide, a potent inhibitor of HRP greatly reduced the response of the HRP-Au sol modified electrode to $H_2O_2$.

The response of the HRP-modified electrodes to $H_2O_2$ is clearly due to the enzyme-catalyzed reduction of $H_2O_2$ at the electrode surface. Electrodes with no HRP (bare glassy carbon, bare gold on glass, Au sol deposited on glassy carbon, Au sol deposited on gold on glass) gave no response to $H_2O_2$. The response of HRP-Au modified electrodes was virtually eliminated by the addition of the HRP inhibitor sodium azide to the analyte solution (see FIG. 3). This demonstrated that catalytically active enzyme is an essential component of these electrodes.

EXAMPLE 5

This example illustrates several versions of a mediator-free glucose sensor. One version, in which glucose oxidase is free in solution, shows good response, while some versions in which both GOD and HRP are immobilized give a poor response.

Determination of Glucose

HRP-Au sol having 9.8 mg Au/ml was prepared as in Example 2. 3 $\mu$l of HRP-Au sol with monolayer surface covering of the sol particles was coated over a 7 mm$^2$ square glassy carbon electrode surface. A coplanar 3-electrode setup, previously described herein, was employed with a 100 $\mu$l sample in pH 7.0 phosphate buffer containing 2 mM KCl. The working electrode was adjusted to 0V/Ag/AgCl to minimize background current. The sample solution was briefly stirred after each addition of glucose but otherwise undisturbed. Steady state current was measured after each glucose addition.

Before measurements were taken, the electrode with immobilized HRP/colloidal gold was rinsed with water before adding 100 $\mu$l buffer and 3 $\mu$l of 35 mg/ml glucose oxidase. The current was measured and recorded as background current. 3–5 $\mu$l of a 5 mM or a 100 mM glucose solution were added with mixing and steady state currents recorded. Response to added glucose was good with a linear range up to 2 mM glucose. The response time was slow, taking several minutes to reach a steady state value.

Measurement of Glucose with HRP-Au-GOD Electrode

An electrode was prepared as in Example 2 except that 2 $\mu$l of glucose oxidase (GOD), 35 mg/ml, was added to the HRP-Au sol before evaporation onto a glassy carbon surface. Response to either peroxide or glucose was poor without a mediator.

A second HRP-Au-GOD electrode was prepared by forming separately two layers of the respective enzymes, both initially adsorbed to colloidal gold. GOD-Au was prepared by adding 2 μl of 35 mg/ml GOD to 30 μl of 9.8 mg/ml colloidal gold sol. The GOD-Au sol was evaporated onto a glassy carbon surface, followed by evaporation of HRP-Au sol onto the GOD-Au layer. This preparation gave a poor signal current in response to glucose or hydrogen peroxide without a mediator.

EXAMPLE 6

A two-step immobilization method with a GOD layer exposed to the analyte in solution and a HRP underlying layer provided a novel electrode with a rapid response and high sensitivity to glucose.

Glucose Measurement With Dual Layer HRP/GOD Colloidal Gold Electrode

HRP-Au and GOD-Au were prepared as in Example 5. HRP/Au was first deposited onto the carbon surface, followed by evaporation of the GOD/Au. The resulting surface was bright gold in color and was stable toward washing. When glucose was added to the solution, using the protocol of Example 5, response time was less than 1 min. Sensitivity was 2.5 nA/μM in the linear range of 30-300 μM glucose. Continuous operation over a period of 40 min resulted in a 20% decrease in signal.

Figure 5:
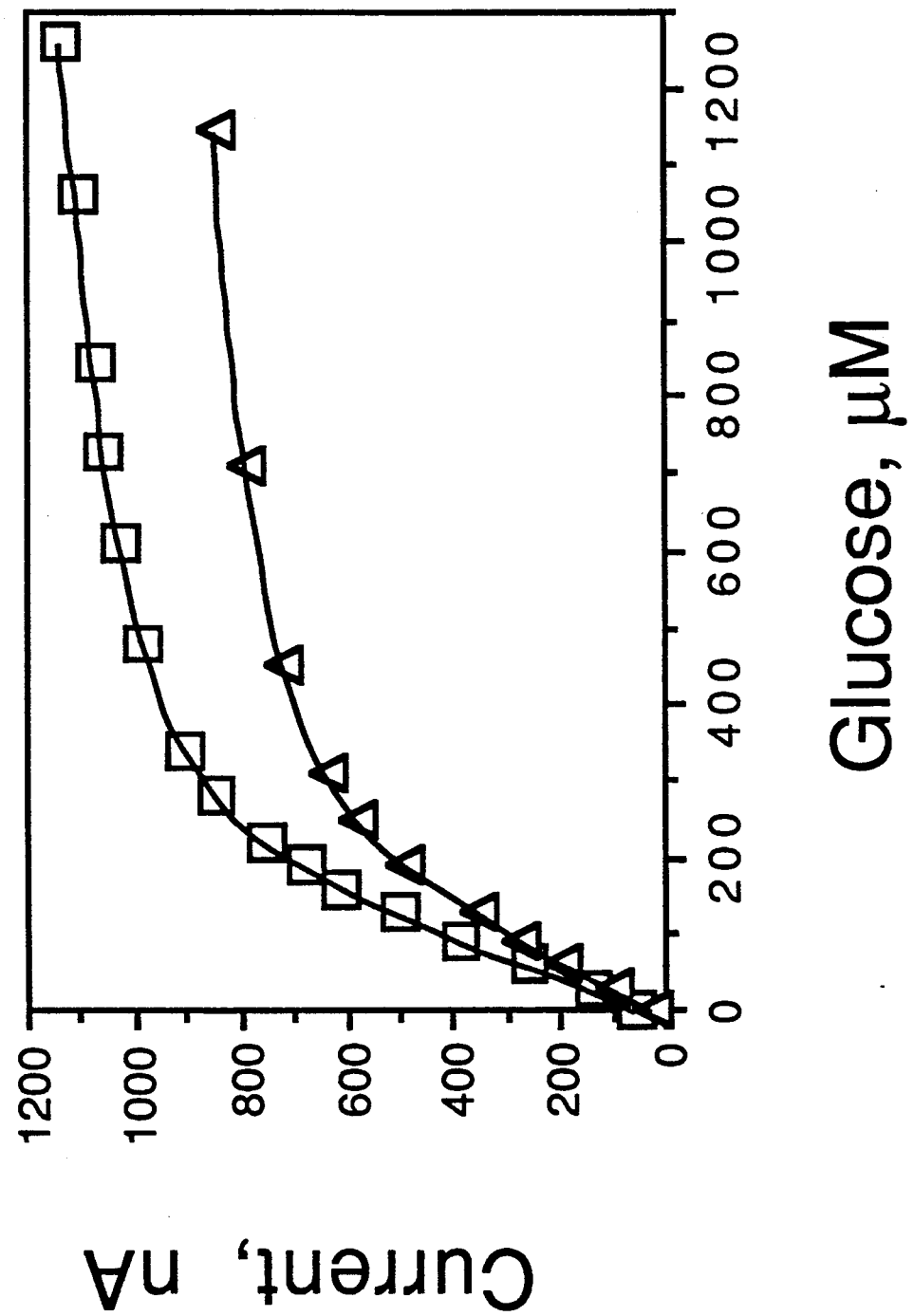
FIG. 5 shows current generated relative to glucose concentration. The detecting bioelectrode was constructed from a colloidal gold/HRP deposited layer underneath a colloidal gold glucose oxidase layer. Measurements were made in a microcell without a mediator. The effect of pH (acetate (Δ) and phosphate (□) buffers) is indicated.
Figure 6:
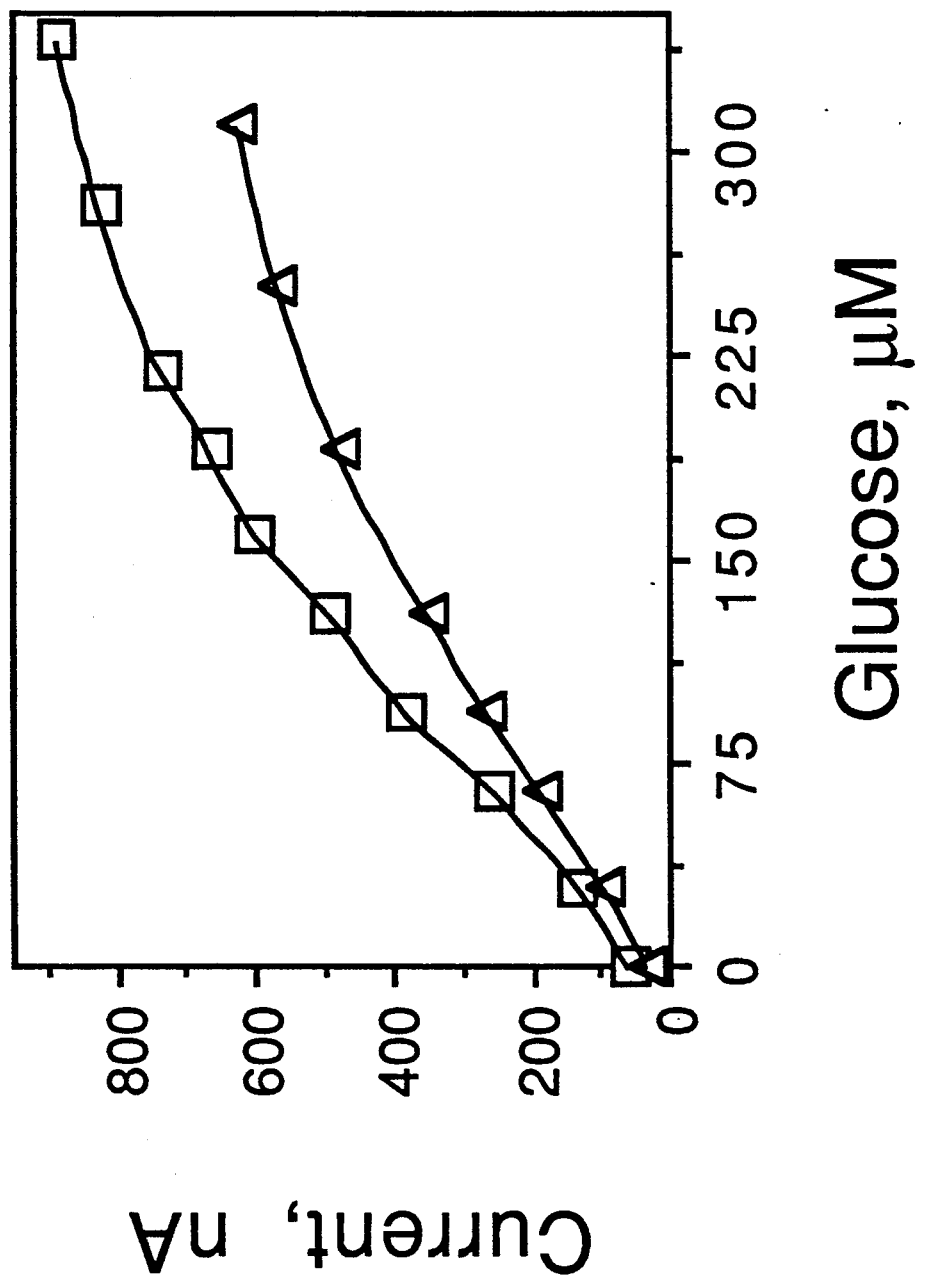
FIG. 6 is an amplified portion of the plot shown in FIG. 5 in the region up to 300 $\mu M$ glucose concentration.

FIG. 5 shows the response of the HRP-Au/GOD-Au electrode to glucose in acetate buffer, pH 5.0 (Δ), and in phosphate buffer, pH 7.0 (□). The range is linear to about 300 μM glucose, shown in FIG. 6 as taken from the linear range shown in FIG. 5.

EXAMPLE 7

This example illustrates one of several potential uses of the biosensors of the present invention. In this example, utilizing a glucose biosensor, some straightforward methods of sample preparation are indicated for potential use in measuring glucose in blood.

Measurement of Glucose in Blood

A blood sample is collected and immediately diluted with phosphate (pH 7.0) or acetate buffer, pH 5.0, 100-1000 fold. Normal blood sugar levels are in the range of about 8 mM, but may be higher after glucose challenge or in diabetics. Alternatively, electrodes may be prepared in accordance with Example 6 but with the addition of a diffusion layer on the electrode surface above the GOD-Au layer. The thickness of the diffusion layer will determine access of glucose to GOD at an appropriate concentration. In other alternatives, GOD or GOD-Au may be immobilized on the surface of a dialysis membrane which is then laid on the HRP-Au layer.

Glucose is then determined as in Example 6.

REFERENCES

The references listed below are incorporated here in by reference to the extent that they supplement, explain, provide a background for or teach methodology, techniques, and/or compositions employed herein.

Albery, W. J., M. J. Eddowes, H. A. O. Hill and A. R. Hillman, *J. Am. Chem. Soc.*, 103 (1981) 3904.

Armstrong, F. A., *Perspectives on Bioinorganic Chemistry*, 1 (1991) 141.

Armstrong, F. A., and A. M. Lannon, *J. Am. Chem. Soc.*, 109 (1987) 7211.

Bowden, E. F., F. M. Hawkridge, and H. N. Blount, *J. Electroanal. Chem.*, 161 (1984) 355.

Cass, A. E. G., ed., *Biosensors; A practical Approach*, Oxford University Press, Oxford/New York, 1990.

Fair, B. D., and A. M. Jamieson, *J. Colloid Interface Sci.*, 77 (1980) 525.

Frew, J. E., M. A. Harmer, H. A. O. Hill, and S. I. Libor, *J. Electroanal. Chem.*, 201 (1986) 1.

Govindaraju, K., B. U. Nair, T. Ramasani, and D. Ramaswamy, *J. Inorg. Biochem.*, 29 (1987) 111.

Gregg, B. A. and Heller, A., *Anal. Chem.* 62, 258-263 (1990).

Guo, L. H., H. A. O. Hill, G. A. Lawrance, G. S. Sanghera and D. Hopper, J., *J. Electranal Chem.*, 266 (1989) 379.

Guo, L. H., H. A. O. Hill, D. J. Hopper, G. A. Lawrance, and G. S. Sanghera, *J. Biol. Chem.*, 265 (1990) 1958.

Guo, L. H., and H. A. O. Hill in A. G. Kykes (ed.), *Adv. Inorg. Chem.*, Vol. 36, Academic Press, New York, 1991, p. 341.

Hagen, W. R., Rur., *J. Biochem.*, 182 (1989) 523.

Hale, P. D., Boguslavsky, L. I., Karan, T. I., Lee, H. S., Skotheim, T. A. and Okamoto, Y., *Anal. Chem.* 63, 677-682, 1991.

Henkens, R. W., Kitchell B. S., O'Daly, S. P., and Crumbliss, A. L., *Rec. Trav. Chem. Pays Bas.* 106, 298 (1987).

Henkens, R. W., O'Daly, S. P., Perine, S. C., Stoneheurner, S. G., Tubergen, V. R., and Crumbliss, A. L., *J. Inorg. Biochem.* 43, 120 (1991).

Joensson, G., and L. Gorton, *Electroanalysis* (N.Y.), 1 (1989) 465.

Nakamoto, S., U.S. Pat. No. 5,082,786, Jan. 21, 1992.

Paddock, R. M., and E. F. Bowden, *J. Electroanal. Chem.*, 260 (1989) 487.

Rishpon, J., Zawodzinski, T. A. and Gottesfeld, S., U.S. Pat. No. 5,082,550, Jan. 21, 1992

What is claimed is:

1. A bioelectrode comprising:
   a conducting surface;
   a peroxidase adsorbed in a monolayer or close to a monolayer onto colloidal gold particles wherein the colloidal gold-adsorbed peroxidase is deposited on the conducting surface; and
   an oxidase layer atop the deposited colloidal gold adsorbed peroxidase wherein direct electron transfer to the conducting surface occurs in the presence of an analyte when the bioelectrode is suitably coupled with a reference/counter electrode.

2. The biooelectrode of claim 1 wherein the peroxidase is horseradish peroxidase.

3. The bioelectrode of claim 1 wherein colloidal gold adsorbed oxidase is deposited atop the peroxidase.

4. The bioelectrode of claim 1 wherein the oxidase is cholesterol oxidase, xanthine oxidase, amino acid oxidase, lactic acid oxidase, alcohol oxidase, glycolate oxidase, pyridoxal-4-oxidase, sorbose oxidase, gulonolactose oxidase or galactose oxidase.

5. The bioelectrode of claim 1 wherein the oxidase is glucose oxidase.

6. The bioelectrode of claim 1 wherein the oxidase is immobilized in a matrix at the conducting surface of the electrode.

7. The bioelectrode of claim 6 wherein the matrix is a hydrophilic polymer.

8. The bioelectrode of claim 7 wherein the hydrophilic polymer is carrageenan.

9. A bioelectrode for mediatorless electrochemical detection of glucose comprising a conducting surface having a first deposited layer of monolayer-coated colloidal gold-adsorbed horseradish peroxidase and a second deposited layer of colloidal gold-adsorbed glucose oxidase atop said first layer.

10. The bioelectrode of claim 9 wherein the conducting electrode surface is glassy carbon.

11. The bioelectrode of claim 9 wherein the first layer of colloidal gold-adsorbed horseradish peroxidase is evaporatively deposited onto the electrode surface prior to evaporative deposition of the second layer of colloidal gold-adsorbed glucose oxidase.

12. The bioelectrode of claim 1 further comprising depositing at least two oxidase enzymes atop the deposited monolayer-coated colloidal gold peroxidase layer.

13. A process for preparing a bioelectrode comprising depositing a coating thickness of between 10 to 20 monolayers of a colloidal gold-adsorbed monolayer of peroxidase onto a conducting surface.

14. A bioelectrode prepared by the process of claim 13.

15. An instrument for measuring concentrations of oxidase substrate comprising the bioelectrode of claim 1.

* * * * *